(12) United States Patent
Yost et al.

(10) Patent No.: US 7,761,159 B2
(45) Date of Patent: Jul. 20, 2010

(54) CARDIAC RHYTHM PACING RATE SELECTION FOR AUTOMATIC CAPTURE THRESHOLD TESTING

(75) Inventors: David William Yost, Brooklyn Park, MN (US); Clayton Scott Foster, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1485 days.

(21) Appl. No.: 11/083,127

(22) Filed: Mar. 16, 2005

(65) Prior Publication Data

US 2006/0212084 A1 Sep. 21, 2006

(51) Int. Cl.
*A61N 1/365* (2006.01)
(52) U.S. Cl. .......................... 607/19; 607/28
(58) Field of Classification Search ....... 607/9, 607/17–20, 21–26, 28
See application file for complete search history.

(56) References Cited

U.S. PATENT DOCUMENTS

| | | | |
|---|---|---|---|
| 6,221,011 B1 | 4/2001 | Bardy | |
| 6,270,457 B1 | 8/2001 | Bardy | |
| 6,275,731 B1 | 8/2001 | Zhu et al. | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 7,079,897 B2 * | 7/2006 | Sun et al. | 607/19 |
| 7,340,303 B2 * | 3/2008 | Zhu | 607/27 |
| 2004/0230244 A1 | 11/2004 | Conley et al. | |

* cited by examiner

*Primary Examiner*—Mark W Bockelman
(74) *Attorney, Agent, or Firm*—Hollingsworth & Funk, LLC (57) ABSTRACT

Cardiac devices and methods that select pacing rates for automatic threshold tests based on a patient's hemodynamic need. A sensor-indicated pacing rate corresponding to a patient's hemodynamic need is determined. A test pacing rate is selected from either the sensor-indicated rate or another rate. Capture threshold testing is performed using the selected pacing rate.

21 Claims, 5 Drawing Sheets

CARDIAC RHYTHM PACING RATE SELECTION FOR AUTOMATIC CAPTURE THRESHOLD TESTING

FIELD OF THE INVENTION

The present invention relates generally to implantable medical devices and, more particularly, to cardiac devices and methods that select cardiac rhythm pacing rates for automatic threshold tests based on a patient's hemodynamic need.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter. Detecting if a pacing pulse "captures" the heart and produces a contraction allows the cardiac rhythm management system to adjust the energy level of pace pulses to correspond to the optimum energy expenditure that reliably produces capture.

SUMMARY OF THE INVENTION

The present invention is directed to various cardiac devices and methods that select cardiac rhythm pacing rates for automatic threshold tests based on a patient's hemodynamic need. In accordance with an embodiment of the present invention, a sensor-indicated pacing rate corresponding to a patient's sensed hemodynamic need is determined. A test pacing rate is selected from one of the sensor-indicated pacing rate and a non-sensor-indicated pacing rate. A capture threshold test is performed using the test pacing rate.

For example, the sensor-indicated pacing rate may be selected if the sensor-indicated pacing rate is greater than the non-sensor-indicated pacing rate. The non-sensor-indicated pacing rate may be selected if the non-sensor-indicated pacing rate is greater than the sensor-indicated pacing rate. The test pacing rate may be selected based on the heart rate before the capture threshold test.

One of the sensor-indicated pacing rate and a predetermined pacing rate may be selected if a current pacing mode is a tracking mode, or one of the sensor-indicated pacing rate and a pacing rate determined based on the heart rate before the capture threshold test may be selected if the current pacing mode is a non-tracking mode. A shortened AV-delay may be used if the current pacing mode is a tracking mode.

Selecting the test pacing rate may involve selecting the test pacing rate to reduce fusion beats and/or to increase the likelihood of captured beats during the capture threshold test. Selecting the test pacing rate may involve selecting the test pacing rate to reduce a pacing rate change when the capture threshold test is initiated. Selecting the test pacing rate may involve selecting the test pacing rate to reduce a pacing rate change when the capture threshold test is initiated and/or terminated. Performing the capture threshold test using the test pacing rate may involve adapting the test pacing rate to meet the patient's hemodynamic need. Performing the capture threshold test using the test pacing rate may involve delivering pacing pulses at the test pacing rate, sensing cardiac signals respectively following the pacing pulses, and determining a capture threshold based on the sensed cardiac signals.

Embodiments of a cardiac rhythm management system in accordance with the present invention are directed to patient internal medical devices having a sensing system configured to sense cardiac signals. A processor is coupled to the sensing system, the processor configured to determine a sensor-indicated pacing rate corresponding to a patient's sensed hemodynamic need. The processor may select a test pacing rate from one of the sensor-indicated pacing rate and a non-sensor-indicated pacing rate, and perform a capture threshold test using the test pacing rate.

The processor may further be configured to select the sensor-indicated pacing rate if the sensor-indicated pacing rate is greater than the non-sensor-indicated pacing rate, and select the non-sensor-indicated pacing rate if the non-sensor-indicated pacing rate is greater than the sensor-indicated pacing rate. The processor may also be configured to select one of the sensor-indicated pacing rate and a predetermined pacing rate if a current pacing mode comprises a tracking mode, and select one of the sensor-indicated pacing rate and a pacing rate determined based on the heart rate before the capture threshold test if the current pacing mode comprises a non-tracking mode.

The processor may be configured to use a shortened AV-delay if the current pacing mode is a tracking mode. The processor may be configured to select the test pacing rate that reduces a pacing rate change when the capture threshold test is initiated and/or terminated.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Devices and methods in accordance with the present invention select cardiac rhythm pacing rates for automatic threshold tests based on a patient's hemodynamic need. If a pacing rate used for a threshold test is selectable, significant differences between the capture threshold test rate and the rate previous to or after the test may be mitigated, thereby reducing the likelihood of fusion and/or pseudofusion beats interfering with the capture threshold detection.

To encourage capture, and discourage fusion, a shortened A-V delay may be used in tracking pacing modes and overpacing may be used in non-tracking pacing modes. In either case a pacing rate may be established for the threshold test that cardiac therapy devices. Rate adaptive pacing features may be incorporated in a variety of cardiac therapy devices, including, for example, implantable cardiac pacemakers, cardioverters, defibrillators, resynchronizers, and other cardiac therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac rhythm management (CRM) devices, such as those listed above. A CRM device implemented in accordance with the present invention may incorporate one or more of the electrode types identified above and/or combinations thereof.

For CRM devices using tracking modes, one concern is that the patient may experience a significant rate swing when switching to and from the automatic threshold test. For CRM devices using non-tracking modes concerns are both the rate swing described above, as well as ensuring over-pacing. Selectable threshold test pacing rates in accordance with the present invention provides methods for establishing threshold test pacing rates that are independent of rate-modification features of a CRM device.

Those skilled in the art will appreciate that reference to a capture threshold procedure indicates a method of determining the capture threshold in one of left atrium, right atrium, left ventricle, right ventricle, or in any combination of heart chambers, e.g., left and right atria and/or left and right ventricles. In such a procedure, the pacemaker, automatically or upon command, initiates a search for the capture threshold of the selected heart chamber or chambers.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. The pacemaker may increase the stimulation energy in discrete steps until a predetermined number of capture events occur to confirm the capture threshold. A capture threshold test may be performed using adaptive safety back up pacing methods of the present invention.

Other procedures for implementing capture threshold testing may be utilized. In one example, the pacing energy may be increased in discrete steps until capture is detected. In another example, the pacing energy may be adjusted according to a binomial or other search pattern.

Consider, for example, threshold tests that may be initiated manually via an external device (for example a commanded test), or automatically initiated on a regular interval (for example, an automatic ambulatory test every 21 hours). The ambulatory tests results may be used either for trending only, or trended and directly applied for pacing output determination, otherwise the auto threshold feature may be off.

For ambulatory threshold tests, when no rate modifiers are on, the pacing rate may be set at a lower rate limit (LRL) in tracking mode, or set at pre-capture threshold test heart rate+10 beats per minute (bpm) in non-tracking mode. If rate modifier options are on, the modification of the device LRL may cause significant differences in the actual pacing rate when switching to and from the automatic threshold test if selectable pacing rates in accordance with the present invention are not utilized.

The present invention addresses this problem in one embodiment using a pseudo LRL approach, without actually changing the device's LRL. The pseudo LRL may be set to off (i.e. the true LRL is used) in device brady parameter settings in tracking mode, or set to pre-capture threshold test heart rate+10 bpm in non-tracking mode. The paced rate during a threshold test may be selected to be the greater of the pseudo LRL and the rate modifier determined rate. In this way, the automatic threshold may be turned on with minimum impact on the rate modifier feature. The heart rate before the capture threshold test may be an average of ten beats (any combination of senses and paces) determined before the threshold test initialization is started. If rate modifiers are set to on, a rate-too-high check may be incorporated after every pace.

Figure 1:
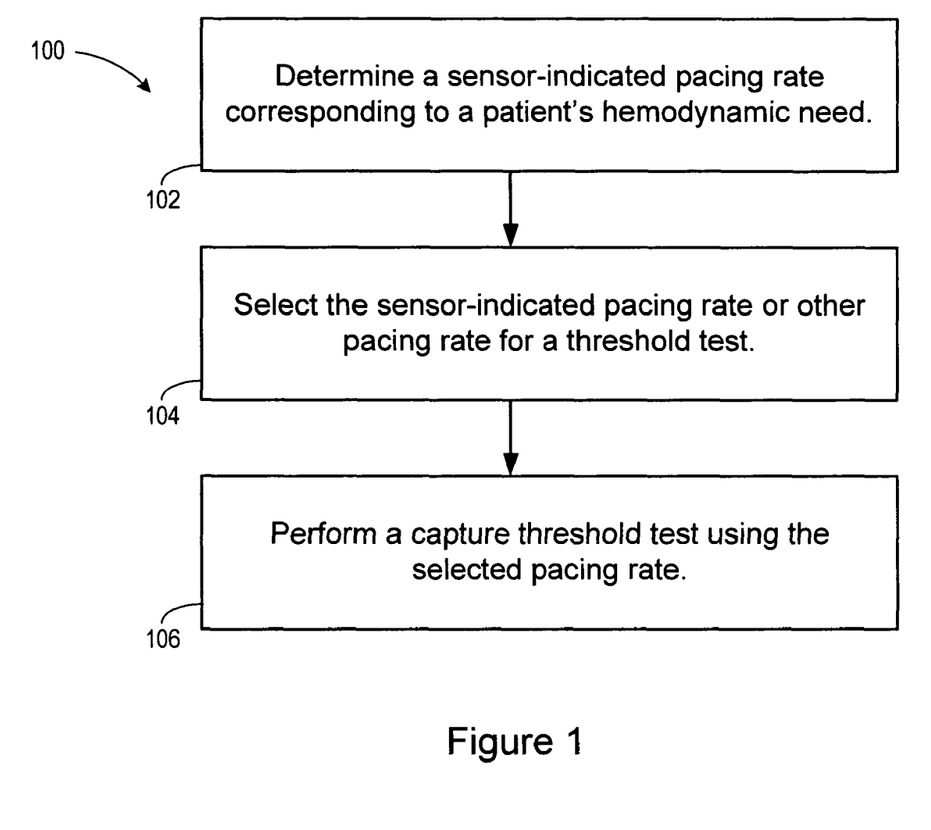
FIGS. 1-3 are flowcharts of methods of selecting pacing rates for capture threshold testing in accordance with embodiments of the present invention.

FIG. 1 is a flowchart of a method 100 of selecting pacing rates for threshold testing in accordance with an embodiment of the present invention. A sensor-indicated pacing rate corresponding to a patient's sensed hemodynamic need is determined 102. A test pacing rate is selected 104 from one of the sensor-indicated pacing rate and a non-sensor-indicated pacing rate. A capture threshold test is performed 106 using the test pacing rate.

One of the sensor-indicated pacing rate and a predetermined pacing rate may be selected if a current pacing mode is a tracking mode, or one of the sensor-indicated pacing rate and a pacing rate determined based on the heart rate before the capture threshold test may be selected if the current pacing mode is a non-tracking mode. A shortened AV-delay may be used if the current pacing mode is a tracking mode.

Figure 2:
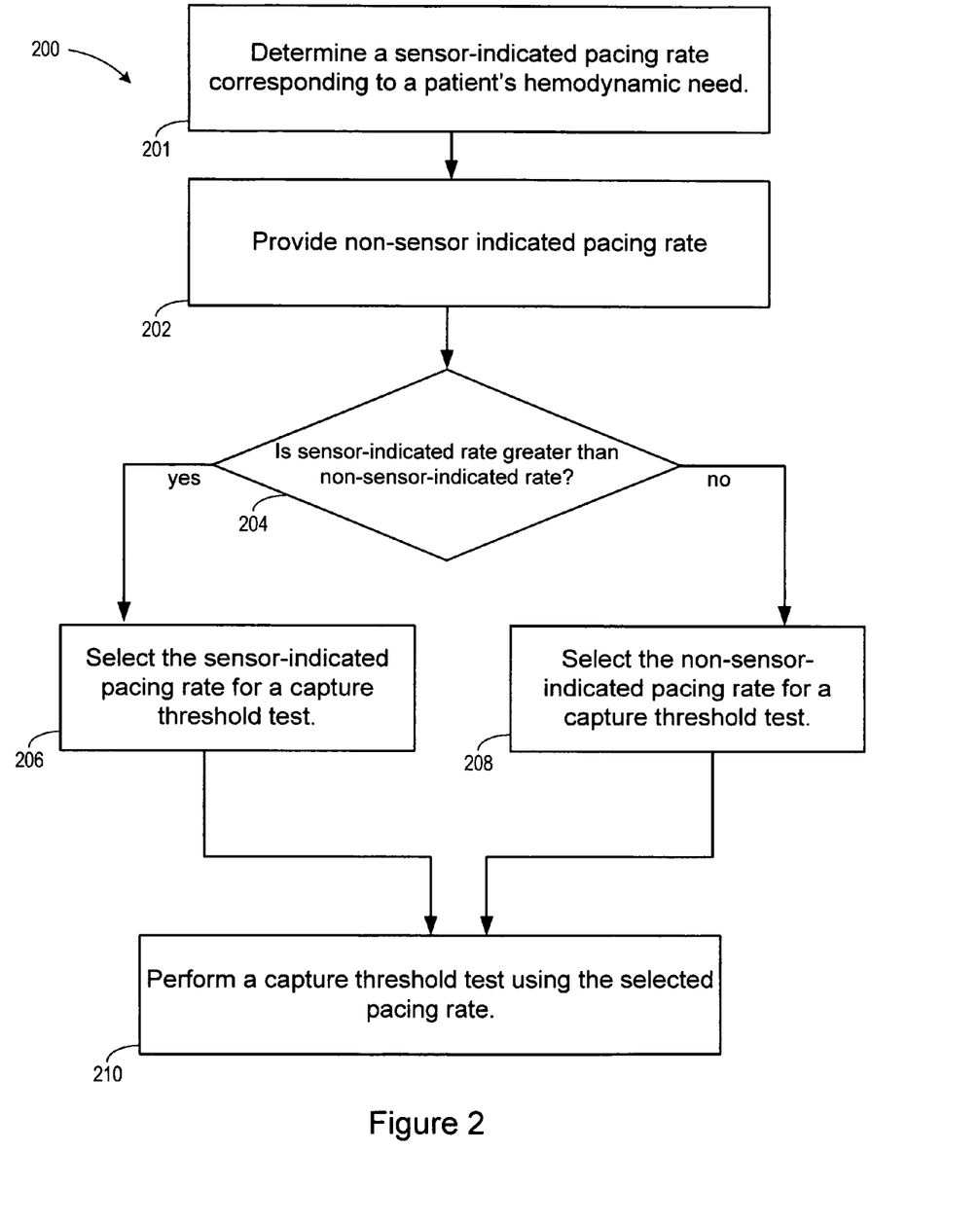

FIG. 2 is a flowchart of a method 200 of selecting pacing rates for threshold testing in accordance with another embodiment of the present invention. A sensor-indicated pacing rate corresponding to a patient's sensed hemodynamic need is determined 201. A non-sensor-indicated rate is provided 202. A decision 204 is made to check if the sensor indicated rate 202 is greater than the non-sensor indicated rate, such as a predetermined LRL, for example. If the sensor-indicated rate is greater than the other rate, the sensor-indicated pacing rate may be selected 206. If the sensor-indicated pacing rate is less than the other rate, then the other rate may be selected 208. A capture threshold test is performed 210 using the selected pacing rate.

Figure 3:
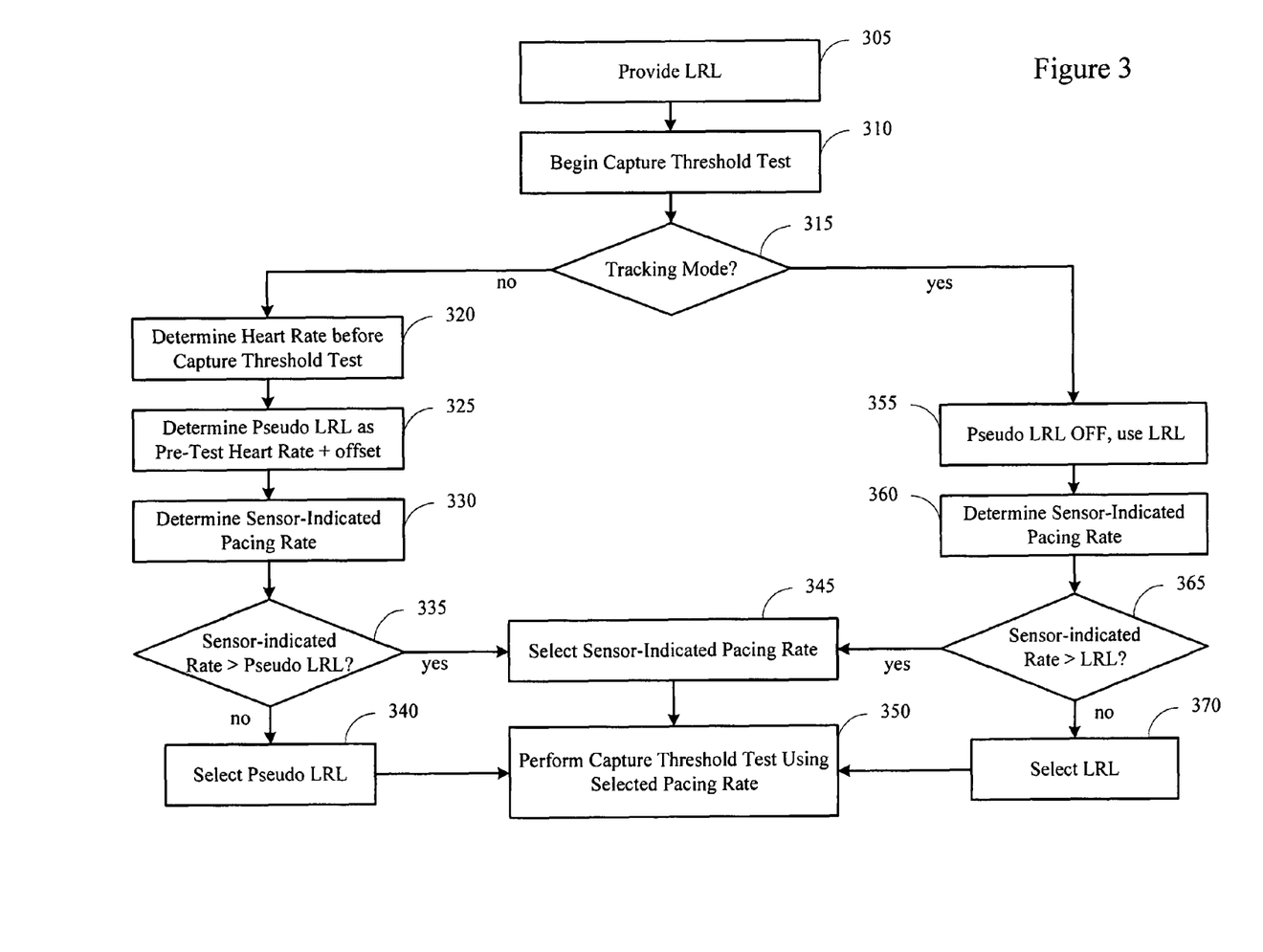

In various embodiments, the non-sensor-indicated pacing rate may comprise the device lower rate limit (LRL) or a pseudo LRL. In some implementations, the pseudo LRL may be calculated as the heart rate before the capture threshold test+ a predetermined offset, such as about 10 bpm. FIG. 3 illustrates a method for selecting the test pacing rate between a sensor-indicated pacing rate and a pseudo-LRL for non-tracking pacing modes, and between the sensor-indicated pacing rate and the device LRL for tracking pacing modes.

A cardiac pacing device incorporates 305 a lower rate limit (LRL), which may be a programmable rate. The LRL represents the lowest rate the device normally uses for pacing. The lower rate limit may also be used in conjunction with rate adaptive pacing, wherein the device calculates the increase above the LRL in beats per minute that is required to meet the patient's hemodynamic need.

A capture threshold is initiated 310. Capture threshold testing may be performed regularly or as needed. In one scenario, a capture threshold test may be performed periodically once every 21 hours, for example. If the cardiac pacing device is operating 315 in a tracking mode, the test pacing rate is selected as shown in process blocks 345-370. If the cardiac pacing device is operating 315 in a non-tracking mode, the capture the test pacing rate is selected as shown in process blocks 320-345.

If the cardiac pacing device is operating 315 in a non-tracking pacing mode, the heart rate before the capture threshold test is determined 320. A pseudo-LRL may be calculated 325 as the pre-capture threshold test heart rate plus offset, such as about 10 bpm.

The sensor-indicated pacing rate is determined 330. If the sensor-indicated rate is greater than 335 the pseudo LRL, then the sensor-indicated pacing rate is selected 345 as the test pacing rate. If the sensor-indicated pacing rate is not greater than 335 the pseudo LRL, then the pseudo LRL is selected 340 as the test pacing rate.

If the cardiac pacing device is operating 315 in a tracking pacing mode, the pseudo LRL is turned OFF 355 and the test pacing rate is selected between the sensor-indicated pacing rate and the LRL. The sensor-indicated pacing rate is determined 360.

If the sensor-indicated rate is greater than 365 the LRL, then the sensor-indicated pacing rate is selected 345 as the test pacing rate. If the sensor-indicated pacing rate is not greater than 365 the LRL, then the LRL is selected 370 as the test pacing rate.

The capture threshold test is performed 350 using the selected test pacing rate. As previously discussed, capture threshold testing involves pacing the heart and determining the cardiac response to pacing. Various methods are available for determining the cardiac response to pacing. Cardiac response classification techniques, aspects of which may be utilized in capture threshold testing using test pacing rate selection employed in various embodiments of the present invention are described in the following commonly owned U.S. Pat. Nos. 7,191,004; 7,162,301; 7,319,900; and U.S. Publication Nos.: 2005/0131477; and 2005/0131478, all of which are incorporated herein by reference.

The embodiments of the present system illustrated herein are generally described as being implemented in a cardiac rhythm management system (CRM) such as an implantable cardiac pacemaker/defibrillator that may operate in numerous pacing modes known in the art. Various types of single and multiple chamber implantable cardiac defibrillators are known in the art and may be used in connection with cardiac devices and methods that provide selectable pacing rates for threshold testing in accordance with the present invention. The methods of the present invention may also be implemented in a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 4:
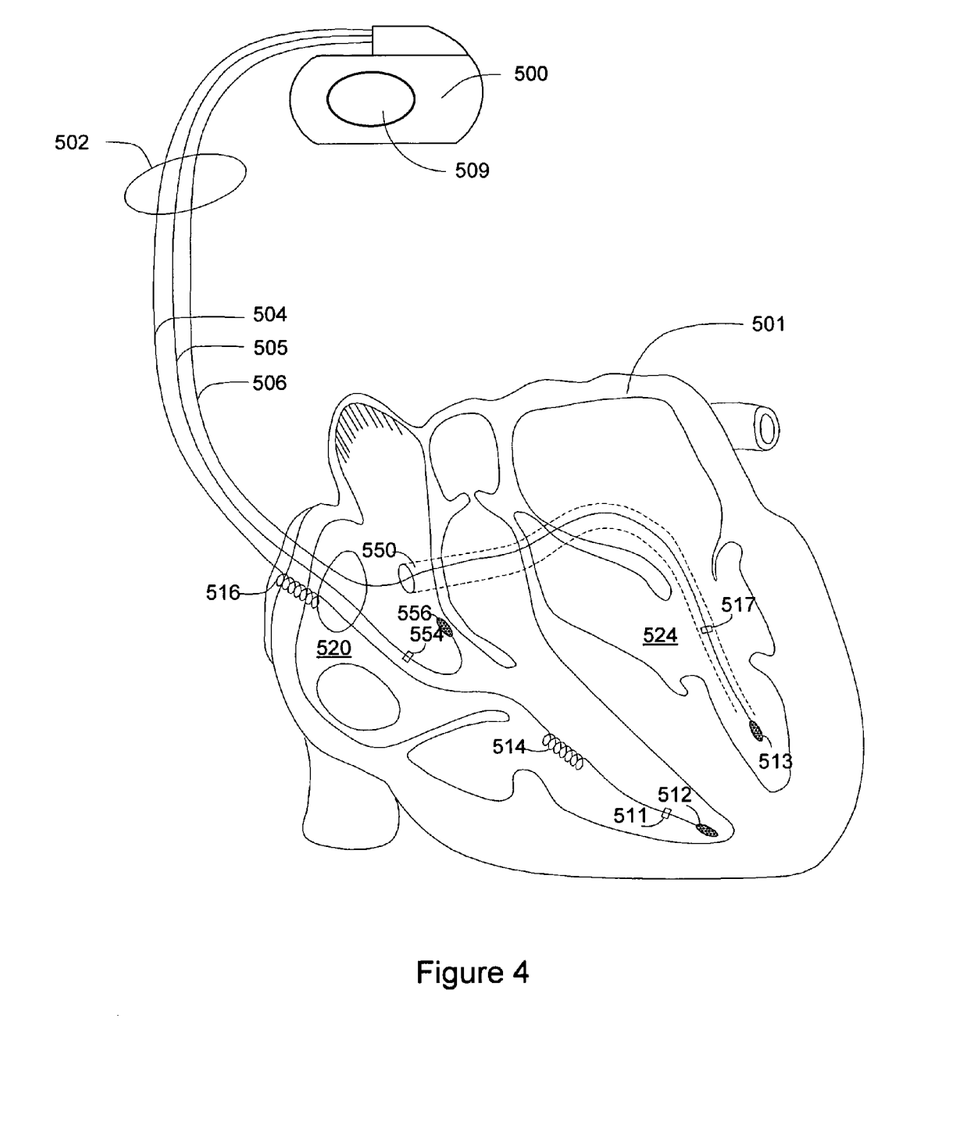
FIG. 4 is a partial view of one embodiment of an implantable medical device that may be used in connection with selection of pacing rates for capture threshold testing in accordance with embodiments of the invention.

FIG. 4 is a partial view of a cardiac rhythm management (CRM) device that may be used to implement pacing rate adjustments based on sleep/wake cycle in accordance with embodiments of the invention. Methods of the invention may be implemented in a variety of implantable or patient-external cardiac therapeutic and/or diagnostic devices including, for example, pacemakers, pacemaker/defibrillators, bi-ventricular pacemakers, and/or cardiac resynchronization devices, among others. The CRM device illustrated in FIG. 4 includes an implantable housing 500 containing circuitry electrically coupled to an intracardiac lead system 502. Portions of the implantable housing may be configured as a can electrode 509. The housing 500 and the intracardiac lead system 502 are implanted in a human body with portions of the intracardiac lead system 502 inserted into a heart 501. The intracardiac lead system 502 is used to detect electric cardiac signals produced by the heart 501 and to provide electrical energy to the heart 501 under predetermined conditions to treat cardiac arrhythmias.

The intracardiac lead system 502 includes one or more electrodes used for pacing, sensing, and/or defibrillation. In the particular embodiment shown in FIG. 4, the intracardiac lead system 502 includes a right ventricular lead system 504, a right atrial lead system 505, and a left ventricular lead system 506. In one embodiment, the right ventricular lead system 504 is configured as an integrated bipolar pace/shock lead.

The right ventricular lead system 504 includes an SVC-coil 516, an RV-coil 514, and an RV-tip electrode 512. The RV-coil 514, which may alternatively be configured as an RV-ring electrode 511 and an RV-coil 514, is spaced apart from the RV-tip electrode 512, which is a pacing electrode for the right ventricle.

The right atrial lead system 505 includes a RA-tip electrode 556 and an RA-ring electrode 554. The RA-tip 556 and RA-ring 554 electrodes may provide pacing pulses to the right atrium of the heart and may also be used to detect cardiac signals from the right atrium. In one configuration, the right atrial lead system 505 is configured as a J-lead.

In the configuration of FIG. 4, portions of the intracardiac lead system 502 are shown positioned within the heart 501, with the right ventricular lead system 504 extending through the right atrium and into the right ventricle. Typical locations for placement of the RV-tip electrode 512 are at the right ventricular (RV) apex or the RV outflow tract.

In particular, the RV-tip electrode 512 and RV-coil electrode 514 are positioned at appropriate locations within the right ventricle. The SVC-coil 516 is positioned at an appropriate location within a major vein leading to the right atrium chamber of the heart 501. The RV-coil 514 and SVC-coil 516 depicted in FIG. 4 are defibrillation electrodes.

The left ventricular lead system 506 is advanced through the superior vena cava (SVC), the right atrium 520, the ostium of the coronary sinus, and the coronary sinus 550. The left ventricular lead system 506 is guided through the coronary sinus 550 to a coronary vein of the left ventricle 524. This vein is used as an access pathway for leads to reach the surfaces of the left atrium and the left ventricle that are not directly accessible from the right side of the heart. Lead placement for the left ventricular lead system may be achieved via subclavian vein access and a preformed guiding catheter for insertion of the left ventricular (LV) electrodes 513 and 517 adjacent the left ventricle. In one configuration, the left ventricular lead system 506 is implemented as a single-pass lead.

An LV distal electrode 513, and an LV proximal electrode 517 may be positioned adjacent to the left ventricle. The LV proximal electrode 517 is spaced apart from the LV distal electrode, 513 which is a pacing electrode for the left ventricle. The LV distal 513 and LV proximal 517 electrodes may also be used for sensing the left ventricle.

The lead configurations illustrated in FIG. 4 represent one illustrative example. Additional lead/electrode configurations may include additional and/or alternative intracardiac electrodes and/or epicardial electrodes. For example, in one configuration, an extracardiac lead may be used to position epicardial electrodes adjacent the left atrium for delivering electrical stimulation to the left atrium and/or sensing electrical activity of the left atrium.

Figure 5:
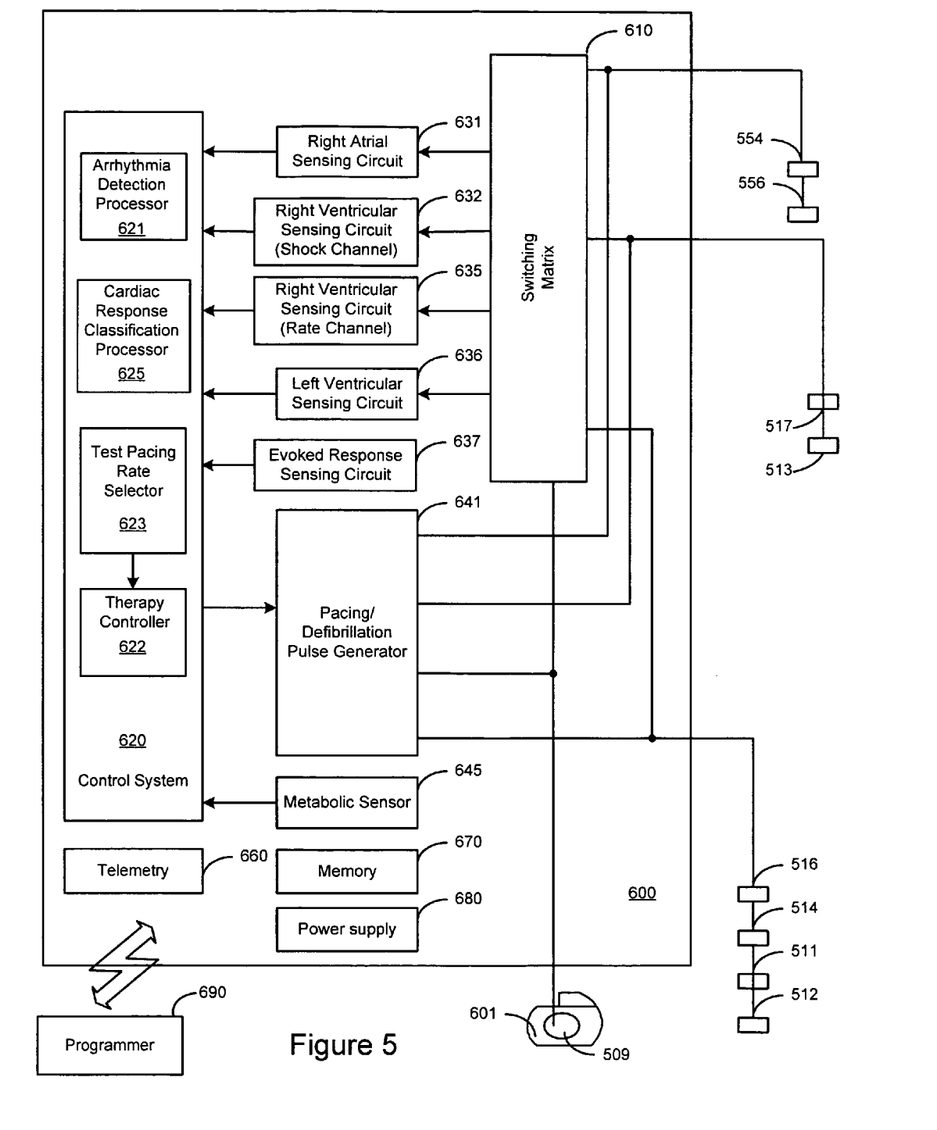
FIG. 5 is a block diagram of an implantable medical device including circuitry for implementing rate adaptive pacing and a pacing rate selector that may be used to determine the pacing rate used for capture threshold testing in accordance with embodiments of the invention.

Referring now to FIG. 5, there is shown a block diagram of a cardiac rhythm management (CRM) device 600 suitable for implementing capture threshold testing pacing rate selection in accordance with embodiments of the invention. FIG. 5 shows a CRM device 600 divided into functional blocks. It is understood by those skilled in the art that there exist many possible configurations in which these functional blocks can be arranged. The example depicted in FIG. 5 is one possible functional arrangement. Various functions of the CRM device 600 may be accomplished by hardware, software, or a combination of hardware and software.

The CRM device 600 includes components for sensing cardiac signals from a heart and delivering therapy, e.g., pacing pulses or defibrillation shocks, to the heart. The circuitry of the CRM device 600 may be encased and hermetically sealed in a housing 601 suitable for implanting in a human body. Power to the circuitry is supplied by an electrochemical battery power supply 680 that is enclosed within the housing 601. A connector block with lead terminals (not shown) is additionally attached to housing 601 to allow for the physical and electrical attachment of the intracardiac lead system conductors to the encased circuitry of the CRM device 600.

In one embodiment, the CRM device 600 comprises programmable microprocessor-based circuitry, including control circuitry 620, a memory circuit 670, sensing circuitry 631, 632, 635, 636, 637 and a pacing/defibrillation pulse generator 641. Components of the CRM device 600 cooperatively perform operations involving test pacing rate selection according to the approaches of the present invention. The control circuitry 620 includes a test pacing rate selector 623 for selecting the test pacing rate used during capture threshold testing. The control system also includes a cardiac response classification processor 625 that determines the cardiac response to pacing during capture threshold testing.

The control circuitry 620 may encompass various additional functional components, for example, an arrhythmia detection processor 621 for detecting cardiac conditions such as bradycardia and tachycardia, and a therapy control unit 622 for controlling delivery of pacing and defibrillation therapy. The therapy control unit 622 controls the pacing rate output during capture threshold testing based on the pacing rate selected by the test pacing rate selector 623.

The memory circuit 670 may store program instructions used to implement the functions of the CRM device 600 as well as data acquired by the CRM device 600. For example, the memory circuit 670 may store historical records of sensed cardiac signals, including arrhythmic episodes, and/or information about therapy delivered to the patient.

The historical data stored in the memory 670 may be used for various purposes, including diagnosis of patient diseases or disorders. Analysis of the historical data may be used to adjust the operations of the CRM device 600. Data stored in the memory 670 may be transmitted to an external programmer unit 690 or other computing device, such as an advanced patient management system as needed or desired.

Telemetry circuitry 660 allows the CRM device 600 to communicate with an external programmer unit 690 and/or other remote devices. In one embodiment, the telemetry circuitry 660 and the external programmer unit 690 use a wire loop antenna and a radio frequency telemetric link to receive and transmit signals. In this manner, programming commands and data may be transferred between the CRM device 600 and the external programmer 690 after implant.

The CRM device 600 may function as a pacemaker and/or a defibrillator. As a pacemaker, the CRM device 600 delivers a series of electrical stimulations to the heart to regulate heart rhythm. Therapy control circuitry 622 controls the delivery of pacing pulses to treat various arrhythmic conditions of the heart, for example. In various embodiments, the CRM device 600 may deliver pacing pulses to one or more of the right atrium, left atrium, right ventricle and the left ventricle. Electrical stimulation pulses may be delivered to the heart to treat tachycardia, bradycardia, and/or to synchronize and/or coordinate contractions of the right and left ventricles or the right and left atria.

Right ventricular pacing may be implemented using unipolar or bipolar configurations. Unipolar RV pacing involves, for example, pacing pulses delivered between the RV-tip 512 to can 509 electrodes. Bipolar pacing involves, for example, delivery of pacing pulses between the RV-tip 512 to RV-coil 514 electrodes. If an RV-ring electrode 511 is present, bipolar pacing may be accomplished by delivering the pacing pulses to the RV-tip 512 and RV-ring 511 electrodes.

Left ventricular pacing may be implemented using unipolar or bipolar configurations. Unipolar LV pacing may include, for example, pacing pulses delivered between the LV distal electrode 513 and the can 509. Alternatively, bipolar LV pacing may be accomplished by delivering the pacing pulses using the LV distal electrode 513 and the LV proximal electrode 517.

Similarly, unipolar (RA-tip electrode 556 to can electrode 509) atrial pacing or bipolar (RA-tip electrode 556 to RA-ring electrode 554) atrial pacing may be provided by the CRM device 600.

In accordance with the present invention, the therapy controller 622 may be programmed to adjust the pacing rate during capture threshold testing of one or more of the right atrium, left atrium, right ventricle and the left ventricle based on the test pacing rate determined by the rate selector 623.

The CRM device 600 may also provide tachyarrhythmia therapy. For example, tachyarrhythmia therapy may be provided in the form of anti-tachycardia pacing (ATP) pulses delivered to the heart. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length. For immediately life threatening arrhythmias, such as ventricular fibrillation, the therapy control circuitry 622 may control the delivery of one or a series of defibrillation shocks to the heart to terminate the fibrillation.

In the embodiment depicted in FIG. 5, electrodes RA-tip 556, RA-ring 554, RV-tip 512, RV-ring 511, RV-coil 514, SVC coil 516, LV distal electrode 513, LV proximal electrode 517, and can 509 are coupled through a switching matrix 610 to various sensing circuits 631, 632, 635, 636, 637. A right atrial sensing channel circuit 631 serves to sense and amplify electrical signals from the right atrium of the heart. For example, bipolar sensing in the right atrium may be implemented by sensing signals developed between the RA-tip 556 and RA-ring 554 electrodes. The switch matrix 610 may be operated to couple the RA-tip 556 and RA-ring 554 electrodes to the RA sensing channel circuit 631 to effect bipolar sensing of right atrial signals. Alternatively, unipolar right atrial sensing may be accomplished by operating the switch matrix 610 to couple the RA-tip 556 and can 509 electrodes to the RA sensing channel circuit 631.

Cardiac signals sensed through the use of the RV-tip electrode 512 are right ventricular (RV) near-field signals and are referred to as RV rate channel signals herein. Bipolar rate channel sensing may be accomplished by operating the switch matrix 610 to couple the RV-tip 512, RV-ring 511 and the RV-coil electrodes 514 through the RV rate channel sensing circuitry 635. The rate channel signal may be detected, for example, as a voltage developed between the RV-tip 512 and the RV-coil 514 electrodes. The RV rate channel sensing circuitry 635 serves to sense and amplify the RV rate channel signal.

Unipolar RV sensing may be implemented, for example, by coupling the RV-tip 512 and can 509 electrodes to the RV rate channel sensing circuitry 635. In this configuration, the rate channel signal is detected as a voltage developed between the RV-tip 512 to can 509 sensing vector.

The RV lead system may also include an RV-ring electrode 511 used for bipolar pacing and sensing. If an RV-ring electrode is included in the lead system, bipolar sensing may be accomplished by sensing a voltage developed between the RV-tip 512 and RV-ring 511 electrodes.

Far-field signals, such as cardiac signals sensed through use of one of the defibrillation coils or electrodes 514, 516 and the can 509, or using both of the defibrillation coils or electrodes 514, 516, are referred to as morphology or shock channel signals herein. The shock channel signal may be detected as a voltage developed between the RV-coil 514 to the can electrode 509, the RV-coil 514 to the SVC-coil 516, or the RV-coil 514 to the can electrode 509 shorted to the SVC-coil 516. The switch matrix 610 is operated to couple the desired shock channel sensing vector, e.g., RV-coil to can, to the right ventricular shock channel sensing circuitry 632. The RV shock channel sensing circuitry 632 serves to sense and amplify the shock channel signal.

The outputs of the switching matrix 610 may also be operated to couple selected combinations of the electrodes to LV sensing channel circuitry 636 for sensing electrical activity of the left ventricle. Bipolar left ventricular sensing may be accomplished by operating the switch matrix 610 to couple the LV-distal 513 and the LV proximal electrodes 517 through the LV channel sensing circuitry 636. In this configuration, the LV signal is detected as a voltage developed between the LV proximal and LV distal electrodes.

Unipolar LV sensing may be implemented, for example, by coupling the LV distal 513 and can 509 electrodes to the LV sensing circuitry 636. In this configuration, the LV signal is detected as a voltage developed between the LV-tip 513 to can 509 sensing vector.

An evoked response sensing circuit 637 may be used to determine the cardiac response to pacing. Various combinations of electrodes 509, 554, 556, 511-517 may be coupled to the evoked response sensing circuit 637 through the switch matrix 610. The cardiac response classification processor 625 may use cardiac signals sensed by the evoked response sensing circuit 637 and/or other sensing circuits 631, 632, 635, 636 to determine the cardiac response to pacing pulses delivered to various chambers of the heart.

The CRM device 600 may incorporate one or more metabolic sensors 645 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer located within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased above a lower rate limit to correspond to the level of activity or rate of respiration.

In accordance with embodiments of the invention, the test pacing rate selector 623 selects between a pacing rate indicated by the metabolic sensor 645 and a non-sensor indicated rate for capture threshold testing.

The components, functionality, and structural configurations depicted herein are intended to provide an understanding of various features and combination of features that may be incorporated in a CRM device. It is understood that a wide variety of CRM devices and other cardiac therapy device configurations are contemplated, ranging from relatively sophisticated to relatively simple designs. As such, particular CRM device, or other cardiac stimulation device configurations may include particular features as described herein, while other such device configurations may exclude particular features described herein.

The CRM device may detect a variety of physiological signals that may be used in connection with various diagnostic, therapeutic or monitoring implementations. For example, the CRM device may include sensors or circuitry for detecting respiratory system signals, cardiac system signals, and signals related to patient activity. In one embodiment, the metabolic sensor of a CRM device senses intrathoracic impedance, from which various respiratory parameters indicative of metabolic need may be derived, including, for example, respiratory tidal volume and minute ventilation. Sensors and associated circuitry may be incorporated in connection with a CRM device for detecting one or more body movement or body posture or position related signals. For example, accelerometers and GPS devices may be employed to detect patient activity, patient location, body orientation, or torso position.

A CRM device of the present invention may be used within the structure of an advanced patient management (APM) system. The advanced patient management system allows physicians to remotely and automatically monitor cardiac and respiratory functions, as well as other patient conditions. In one example, a CRM device implemented as a cardiac pacemaker, defibrillator, or resynchronization device may be equipped with various telecommunications and information technologies that enable real-time data collection, diagnosis, and treatment of the patient. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for performing a capture threshold test with a cardiac pacing device adapted to provide pacing therapy to a heart of a patient, the method comprising:
    providing a non-sensor-indicated pacing rate to the pacing device
    operating the pacing device in a current pacing mode before the capture threshold test;
    determining a sensor-indicated pacing rate corresponding to the patient's sensed hemodynamic need;
    selecting either the sensor-indicated pacing rate or the non-sensor-indicated pacing rate as a test pacing rate;
    switching operation of the pacing device from the current pacing mode to the capture threshold test; and
    performing the capture threshold test using the test pacing rate.

2. The method of claim 1, wherein selecting the test pacing rate comprises:
    selecting the sensor-indicated pacing rate if the sensor-indicated pacing rate is greater than the non-sensor-indicated pacing rate; and
    selecting the non-sensor-indicated pacing rate if the non-sensor-indicated pacing rate is greater than the sensor-indicated pacing rate.

3. The method of claim 1, wherein selecting the test pacing rate comprises selecting one of the sensor-indicated pacing rate and a predetermined pacing rate.

4. The method of claim 1, wherein selecting the test pacing rate comprises selecting one of the sensor-indicated pacing rate and a pacing rate determined based on a heart rate before the capture threshold test.

5. The method of claim 1, wherein selecting the test pacing rate comprises:
    selecting one of the sensor-indicated pacing rate and a predetermined pacing rate if a current pacing mode comprises a tracking mode; and
    selecting one of the sensor-indicated pacing rate and a pacing rate determined based on a heart rate before the capture threshold test if the current pacing mode comprises a non-tracking mode.

6. The method of claim 5, wherein selecting one of the sensor-indicated pacing rate and the predetermined pacing rate comprises using a shortened AV-delay if the current pacing mode comprises a tracking mode.

7. The method of claim 1, wherein selecting the test pacing rate comprises selecting the test pacing rate to reduce fusion beats during the capture threshold test.

8. The method of claim 1, wherein selecting the test pacing rate comprises selecting the test pacing rate to increase a likelihood of captured beats during the capture threshold test.

9. The method of claim 1, wherein the current pacing mode is a rate-adaptive mode, and wherein selecting the test pacing rate comprises selecting the test pacing rate to reduce a pacing rate change when switching from the current pacing mode to the capture threshold test.

10. The method of claim 1, further comprising:
    after the capture threshold test, switching operation of the pacing device from the capture threshold test to a subsequent pacing mode that is a rate-adaptive mode;
    wherein selecting the test pacing rate comprises selecting the test pacing rate to reduce a pacing rate change when switching from the capture threshold test to the subsequent pacing mode.

11. The method of claim 1, wherein performing the capture threshold test using the test pacing rate comprises adapting the test pacing rate to meet the patient's hemodynamic need.

12. The method of claim 1, wherein performing the capture threshold test using the test pacing rate comprises:
    delivering pacing pulses at the test pacing rate;
    sensing cardiac signals respectively following the pacing pulses; and
    determining a capture threshold based on the sensed cardiac signals.

13. The method of claim 1, wherein the non-sensor-indicated pacing rate comprises a lower rate limit.

14. The method of claim 1, wherein the non-sensor-indicated pacing rate comprises a pseudo lower rate limit.

15. The method of claim 1, wherein the non-sensor-indicated pacing rate is based on a measured heart rate.

16. The method of claim 1, wherein the non-sensor-indicated pacing rate comprises a programmable pacing rate.

17. The method of claim 1, wherein the non-sensor-indicated pacing rate comprises a measured heart rate added to a predetermined offset.

18. The method of claim 17, wherein the measured heart rate is determined prior to the capture threshold test based on a predetermined number of sensed and paced beats.

19. The method of claim 1, wherein determining the sensor-indicated pacing rate corresponding to the patient's sensed hemodynamic need comprises determining the sensor-indicated pacing rate based on patient activity.

20. The method of claim 1, wherein determining the sensor-indicated pacing rate corresponding to the patient's sensed hemodynamic need comprises determining the sensor-indicated pacing rate based on patient respiration.

21. The method of claim 1, wherein the selecting is based on whether the current pacing mode is a tracking mode or a non-tracking mode.

* * * * *

UNITED STATES PATENT AND TRADEMARK OFFICE
CERTIFICATE OF CORRECTION

| | | |
|---|---|---|
| PATENT NO. | : 7,761,159 B2 | Page 1 of 1 |
| APPLICATION NO. | : 11/083127 | |
| DATED | : July 20, 2010 | |
| INVENTOR(S) | : Yost et al. | |

It is certified that error appears in the above-identified patent and that said Letters Patent is hereby corrected as shown below:

On the Title page:

Item (22) Filed: "Mar. 16, 2005" should read --Mar. 17, 2005--.

Signed and Sealed this
Twenty-eighth Day of December, 2010

David J. Kappos
*Director of the United States Patent and Trademark Office*